US008889165B2

(12) United States Patent
Bouler et al.

(10) Patent No.: US 8,889,165 B2
(45) Date of Patent: Nov. 18, 2014

(54) INJECTABLE CALCIUM-PHOSPHATE CEMENT RELEASING A BONE RESORPTION INHIBITOR

(75) Inventors: Jean-Michel Bouler, Carquefou (FR); Bruno Bujoli, Suce sur Erdre (FR); Pascal Janvier, Nantes (FR); Ibrahim Khairoun, Nantes (FR); Jean-Noël Argenson, Marseilles (FR)

(73) Assignees: Graftys, Nantes (FR); Centre National de la Recherche Scientifique (C.N.R.S.), Paris (FR)

( * ) Notice: Subject to any disclaimer, the term of this patent is extended or adjusted under 35 U.S.C. 154(b) by 820 days.

(21) Appl. No.: 12/031,562

(22) Filed: Feb. 14, 2008

(65) Prior Publication Data
US 2008/0206296 A1 Aug. 28, 2008

Related U.S. Application Data

(60) Provisional application No. 60/901,090, filed on Feb. 14, 2007.

(30) Foreign Application Priority Data

Feb. 14, 2007 (EP) ..................................... 07290185

(51) Int. Cl.
 *A61F 13/00* (2006.01)
 *A61K 33/42* (2006.01)
 *A61L 24/02* (2006.01)
 *A61L 24/00* (2006.01)

(52) U.S. Cl.
 CPC ............. *A61L 24/0063* (2013.01); *A61L 24/02* (2013.01); *A61L 24/001* (2013.01)
 USPC .......................................... 424/422; 424/602

(58) Field of Classification Search
 None
 See application file for complete search history.

(56) References Cited

U.S. PATENT DOCUMENTS

| 4,880,610 | A | 11/1989 | Constantz |
| 5,053,212 | A | 10/1991 | Constantz et al. |
| 5,683,461 | A | 11/1997 | Lee et al. |
| 5,717,006 | A | 2/1998 | Daculsi et al. |
| 5,733,564 | A | 3/1998 | Lehtinen |
| 5,965,547 | A | 10/1999 | Goodship et al. |
| 2005/0199156 | A1* | 9/2005 | Khairoun et al. ............. 106/690 |
| 2005/0241535 | A1 | 11/2005 | Bohner |
| 2005/0282783 | A1* | 12/2005 | Bujoli et al. .................... 514/89 |

FOREIGN PATENT DOCUMENTS

| EP | 0416761 | 8/1990 |
| EP | 0543765 | 10/1992 |
| EP | 0664133 | 7/1994 |
| WO | WO 96-39107 | * 12/1996 |
| WO | WO-0047214 | 8/2000 |

OTHER PUBLICATIONS

Denissen et. al., Net-shaped hydroxyapatite implants for release of agents modulating peridontal-like tissues, Journal of Periodontal Research, 1997:32: 40-46.*
Denissen H. et al, Net-shaped hydroxyapatite implants for relese of agents modulating periodontal-like tissues, J Peridont Res 1997: 32: 40-46.*
Fernandez, E. et. al., Journal of Materials Science: Materials in Medicine 10 (1999) 223-230.*
Coleman, Robert E., The Oncologist, 5 (2000) pp. 463-470.*
Schnitzer, V., et al., Acta Biomaterialia & (2011) pp. 759-770.*

* cited by examiner

*Primary Examiner* — Brian-Yong Kwon
*Assistant Examiner* — Lyndsey Beckhardt
(74) *Attorney, Agent, or Firm* — Stephen J. Weyer, Esq.; Stites & Harbison, PLLC.

(57) ABSTRACT

The present invention relates to a macroporous, resorbable and injectable apatitic calcium-phosphate cement with a high compressive strength useful as bone cement and releasing a bone resorption inhibitor, preparation method and uses thereof.

10 Claims, 4 Drawing Sheets

INJECTABLE CALCIUM-PHOSPHATE CEMENT RELEASING A BONE RESORPTION INHIBITOR

Figure 1:
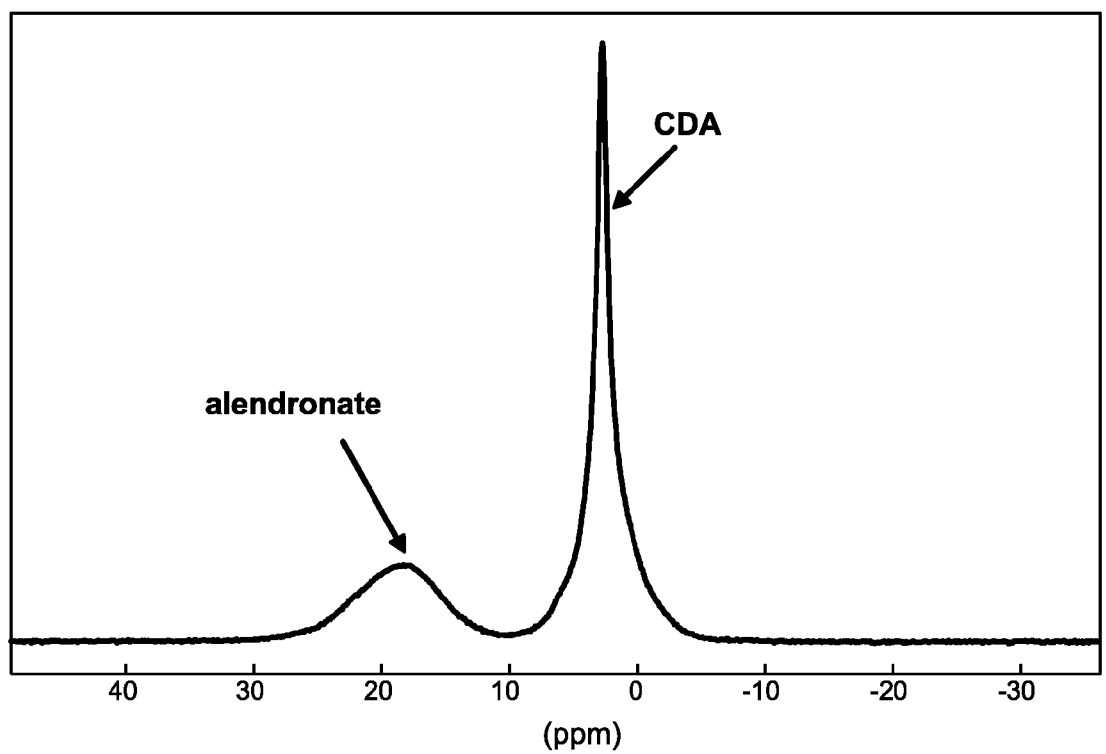

This application claims benefit of U.S. Provisional Application No. 60/901,090, filed Feb. 14, 2007 (which is hereby incorporated by reference).

The invention relates to a macroporous, resorbable and injectable apatitic calcium-phosphate cement with a high compressive strength useful as bone cement and releasing a bone resorption inhibitor.

Bone is a composite of biopolymers, principally collagen, and an inorganic component identified as carbonate hydroxyapatite, approximated as $(Ca,Mg,Na,M)_{10}(PO_4, CO_3, HPO_4)_6(OH,Cl)_2$.

Deregulation of the bone activity of an individual is the cause of many bone pathologies such as osteoporosis, Paget's disease or osteolytic tumors. Taking into account, in particular, the increase in human life expectancy, osteoporosis has become a public health problem and much research has been undertaken to remedy it. Since the bone pathologies under consideration are caused by an imbalance in bone remodeling to the benefit of the activity of the osteoclasts, one of the routes of treatment envisioned consisted in reducing the activity of the osteoclasts, in order to slow down the degradation of the bone material.

Studies performed on various gem-bisphosphonic acids have shown their inhibitory power on osteoclast activity (G. A. Rodan et al., Therapeutic Approaches to Bone Diseases, 1 Sep. 2000, Vol. 289, Science, pp. 1508-1514). The use of some of them as medicaments, especially etidronate, clodronate, pamidronate, alendronate, risedronate, tiludronate and ibandronate, has been approved in various countries. Data have been published for other gem-bisphosphonic acid compounds, especially zoledronate, incadronate, olpadronate and neridronate. The gem-bisphosphonic acids that are used at the present time for the treatment of bone lesions are used systemically and, as a result, give rise to a few undesirable side effects. They can cause renal disorders and jaw osteonecrosis (Eckert A. W., Cancer Treatment Reviews, 2006, in the press) when they are administered intravenously, and digestive system-disorders, especially oesophagi or stomach ulcers, when they are administered orally [(Lin J. H., Bone 1996; 18; 75-85) or (Thiébauld D. et al., Osteoporos Int. 1994; 76-73)]. Another drawback of the oral administration lies in the low level of absorption of the active principle onto bone material.

To date, a wide variety of implant materials have been used to repair, restore, and augment bone. The most commonly used implants include autologous bone, synthetic polymers and inert metals. Protocols using these materials have significant disadvantages that can include patient pain, risk of infection during operations, lack of biocompatibility, cost, and the risk that the inserted hardware can further damage the bone. Therefore, a major goal of biomaterial scientists has been to develop novel bone substitutes that can be used as alternatives to these conventional techniques for skeletal repair.

Bone cements, such as cements based on polymethylmethacrylate (PMMA) offer certain advantages in avoiding the use of solid implants, but also have several disadvantages. Methacrylates and methacrylic acid are known irritants to living tissues, and when PMMA-based cements are cured in vivo, free radicals are generated, which can damage surrounding tissues. Moreover, the polymerization reaction for these materials is highly exothermic, and the heat evolved during curing can damage tissues. In addition, these materials are not biodegradable.

The concept and potential advantages of an apatitic or calcium phosphate cement (CPC) as a possible restorative material was first introduced by LeGeros et al in 1982 ("Apatitic Calcium Phosphates: Possible Restorative Materials", J Dent Res 61 (Spec Iss):343).

There are presently several CPC commercial products. CPC have the following advantages: malleability allowing them to adapt to the defect's site and shape. The introduction of injectable calcium phosphate cements greatly improved the handling and delivery of the cements and opened up areas of new applications for the CPC.

CPC systems consist of a powder and a liquid component. The powder component is usually made up of one or more calcium phosphate compounds with or without additional calcium salts. Other additives are included in small amounts to adjust setting times, increase injectability, reduce cohesion or swelling time, and/or introduce macroporosity.

Such materials are disclosed, for example, in EP 0 416 761, U.S. Pat. No. 4,880,610, U.S. Pat. No. 5,053,212, EP 0 664 133, EP 0 543 765, WO 96/36562, and WO 2004/000374.

FR-2715853 describes compositions for biomaterials for resorption/substitution of support tissues, comprising a mineral phase composed of BCP or calcium-titanium-phosphate, and a liquid aqueous phase comprising an aqueous solution of a cellulose-based polymer. These injectable compositions contain no active principle.

Noninjectable bone substitutes, which are in the form of implants, are also known. For example, H. Denissen et al. (J. Periodontal, Vol. 71, No. 2, February 2000, pp. 280-296) describes implants of hydroxyapatite modified by absorption of a particular gem-bisphosphonic acid, namely (3-dimethylamino-1-hydroxypropylidene)-1,1-bisphosphonic acid, or olpadronate. The in situ release of the acid is said to promote bone reconstruction. However, hydroxyapatite itself has the drawback of being very poorly resorbable.

The international application WO03/074098 describes a modified phosphocalcic compound obtained by the addition of a gem-bisphosphonic acid or an alkali metal or alkaline-earth metal salt thereof to a suspension of a precursor phosphocalcic compound in ultrapure water, by stirring the reaction medium at room temperature, and then recovering the pellet by centrifugation, washing the pellet with ultrapure water, followed by filtering and drying in air at room temperature. WO03/074098 also describes a suspension of the so obtained modified phosphocalcic compound in a solution or an hydrogel and the use of the so obtained injectable composition for the treatment of osteoporosis and osteolytic tumors. The inventors of WO03/074098 thus recommend a local administration of a gem-bisphosphonic acid, the phosphocalcic phase providing a source of calcium and of phosphate required for stimulation of the bone remodelling.

The present applicant has now surprisingly found a method of producing a calcium-phosphate bone cement i.e. an auto-hardening cement, having a compressive strength close to bone, being resorbable for its substitution by new bone material and presenting a release of a gem-bisphosphonic compound, i.e. a bisphosphonic acid or a salt thereof, which allows a regulation of bone remodelling.

First, the present inventors have shown that it is possible to obtain an auto-hardening calcium-phosphate cement comprising a gem-bisphosphonic compound with a setting time suitable for a chirurgical use while said gem-bisphosphonic compound shows a setting retarder activity. Indeed, the phosphonate groups of the gem-bisphosphonic compounds compete with phosphate groups of the cement paste in the following setting reaction. Consequently, the final product, its setting time and hardness are modified.

Mechanism Proposal

In presence of the liquid phase, the initial calcium phosphate compound is partially hydrolysed. $Ca^{2+}$ and $PO_4^{2-}$ ions are released. Bisphosphonic compounds chelate to $Ca^{2+}$ ions and may hamper the apatite precipitation (see reaction below):

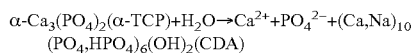

$\alpha\text{-}Ca_3(PO_4)_2(\alpha\text{-TCP}) + H_2O \rightarrow Ca^{2+} + PO_4^{2-} + (Ca,Na)_{10}(PO_4,HPO_4)_6(OH)_2(CDA)$ Second, the present inventors have shown that it is possible to obtain a resorbable calcium-phosphate cement comprising a gem-bisphosphonic compound. This is an unexpected technical effect since the introduction of a gem-bisphosphonic compound was thought to reduce the resorbability potential of phosphocalcic compounds in general.

Third, the present inventors have shown that it is possible to obtain a calcium-phosphate cement releasing a gem-bisphosphonic compound which is thus able to have its inhibitor activity locally on the osteoclasts. This allows solving the secondary effects of an oral administration. Moreover, the dosage used in the cement (for example: 4 mg/implanted site) is much lower than the dosage used for an oral administration (10-70 mg/day during several months). Furthermore, it has been shown (Clin Cancer Res. 2006 15; 12(20 Pt 2):6222s-6230s, Chem Med Chem. 2006 February; 1 (2):267-73) that bone has a very high affinity for gem-bisphosphonic compounds. Thus, the gem-bisphosphonic compounds released by the cement according to the invention will be immediately absorbed by bone close around the implantation site and all the dose released will be trapped.

DEFINITIONS

A "cement" is the result of the setting of a paste resulting from the mixing of a pulverulent solid phase and a liquid phase.

The "setting" of a cement means the hand-off auto-hardening at room or body temperature of the paste resulting from the mixing of the solid phase and the liquid phase.

An "injectable cement" means a cement paste sufficiently fluid to flow through a needle with a diameter of a few millimeters, preferably between 1 and 5 mm.

A "calcium phosphate cement" is a cement wherein the pulverulent solid phase is made of a calcium phosphate compound or a mixture of calcium and/or phosphate compounds.

An "apatitic" calcium phosphate cement crystallises in the hexagonal system having the formula $Ca_{5x}(PO_4)_{3x}(OH,Cl,F)_x$ with $x \geq 1$.

Preparation Methods

Thus, the present invention relates to a method for preparing an injectable calcium-phosphate bone cement releasing a gem-bisphosphonic derivative comprising the addition of a gem-bisphosphonic compound or a calcium precursor modified with a gem-bisphosphonic derivative, in the solid phase or in the liquid phase, wherein the gem-bisphosphonic derivative amount is up to 2.5% by weight in respect to the weight of solid phase.

The gem-bisphosphonic derivative amount and the way to incorporate it in the preparation method according to the invention is an essential feature in order to provide a cement according to the invention with an initial setting time suitable for a surgical use, i.e. lower than 1 hour, preferably lower than 30 min.

The bisphosphonic acids or salts thereof that may be used as gem-bisphosphonic compounds correspond to the formula:

$(OY)(OX)P(O)\text{---}CR_1R_2\text{---}P(O)(OX)(OY)$ wherein X or Y represents, independently of each other, H or an alkali metal or alkaline-earth metal cation, and any organic or inorganic cation of biological interest.

$R_1$ represents H, OH or a halogen, and $R_2$ represents a hydrogen or a halogen, an alkyl radical, an aminoalkyl radical in which the amino group optionally bears an alkyl substituent, an alkylamino radical, an alkyl radical bearing an aromatic substituent comprising at least one N atom, an alkyl radical bearing an aromatic thioether group.

When $R_1$ and/or $R_2$ represent a halogen, Cl is particularly preferred.

When $R_2$ is an alkyl radical, alkyls containing from 1 to 6 carbon atoms are preferred.

When $R_2$ is an aminoalkyl radical, radicals $NH_2(CH_2)_n$— in which n is less than 6 are preferred.

When $R_2$ is an alkylaminoalkyl radical, the preferred radicals are radicals $R'R''N(CH_2)_m$— in which R' and R" represent, independently of each other, H or an alkyl radical containing up to 5 carbon atoms, and m is less than 6.

When R is an alkylamino radical, the radicals RCNH— in which RC is a cycloalkyl containing from 3 to 7 carbon atoms are preferred.

When $R_2$ is an alkyl radical bearing an aromatic substituent comprising at least one N atom, alkyls containing up to 3 carbon atoms and bearing one pyridyl or imidazolyl group are preferred.

When $R_2$ is an alkyl radical bearing an aromatic thioether group, alkyls containing up to 3 carbon atoms and bearing a phenylthio group in which the phenyl group optionally bears a halogen substituent are preferred.

Among these gem-bisphosphonic compounds, mention may be made of:
- etidronate ($R_1$—OH, $R_2$—$CH_3$),
- clodronate ($R_1$—Cl, $R_2$—Cl),
- pamidronate ($R_1$—OH, $R_2$—$CH_2CH_2NH_2$),
- alendronate ($R_1$—OH, $R_2$—$(CH_2)_3NH_2$),
- risedronate ($R_1$—OH, $R_2$—$CH_2$-3-pyridine),
- tiludronate ($R_1$—H, $R_2$—$CH_2$—S—$C_6H_4$—Cl),
- ibandronate ($R_1$—OH, $R_2$—$CH_2$—$CH_2$—$N(CH_3)$pentyl),
- zoledronate ($R_1$—OH, $R_2$—$CH_2$-imidazole),
- incadronate ($R_1$—H, $R_2$—NH-(cycloheptyl)),
- olpadronate ($R_1$—OH, $R_2$—$CH_2$—$CH_2$—$N(CH_3)_2$),
- neridronate ($R_1$—OH, $R_2$—$(CH_2)_5NH_2$).

A salt of a bisphosphonic acid may be an organic or mineral salt, preferably an alkali metal or alkaline-earth metal salt.

In a preferred embodiment, a gem-bisphosphonic compound used in the method according to the invention is selected from the group consisting of etidronate, clodronate, pamidronate, alendronate, risedronate, tiludronate, ibandronate, zoledronate, incadronate, olpadronate, and neridronate.

Three ways may be used to prepare a cement according to the invention:
- The gem-bisphosphonic derivative is dissolved in the cement liquid phase; or
- The gem-bisphosphonic derivative is added at the pulverulent solid phase; or
- The gem-bisphosphonic derivative is chemically associated to a calcium precursor and added in the solid or the liquid phase When the gem-bisphosphonic derivative is dissolved in the cement liquid phase, the gem-bisphosphonic derivative amount is preferably up to 0.3% by weight in respect to the weight of solid phase.

When the gem-bisphosphonic derivative is added at the pulverulent solid phase, the gem-bisphosphonic compound amount is preferably up to 5% by weight in respect to the weight of solid phase.

When the gem-bisphosphonic derivative is chemically associated to a calcium precursor and added in the solid or the liquid phase, the gem-bisphosphonic compound amount is preferably up to 0.15% by weight in respect to the weight of solid phase.

The chemical association of the gem-bisphosphonic compound may be obtained by adding a gem-bisphosphonic acid or an alkali metal or alkaline-earth metal salt or and any organic or inorganic cation of biological interest thereof to a suspension of a precursor phosphocalcic compound, in a solvent preferably an aqueous medium (e.g. ultrapure water), by stirring the reaction medium at room temperature, and then recovering the formed compound by centrifugation. The compound may then be purified by washing with ultrapure water, followed by filtering and drying in air at room temperature.

The calcium precursor is chosen:

(i) from calcium orthophosphates. By way of example, mention may be made of alpha- or beta-tricalcium phosphate (generally denoted as α-TCP, β-TCP), CDA, which is a calcium-deficient hydroxyapatite (obtained, for example, by alkaline hydrolysis of a calcium hydrogen orthophosphate), hydroxyapatite (HA), dicalcium phosphate anhydrous (DCPA), $CaHPO_4$; dicalcium phosphate dihydrate (DCPD), $CaHPO_4.2H_2O$, tetracalcium phosphate (TTCP), $Ca_4P_2O_9$; amorphous calcium phosphate (ACP), $Ca_x(PO_4)y.H_2O$; monocalcium phosphate monohydrate (MCPM), $CaH_4(PO_4)_2.H_2O$; and, ii) non phosphate calcium salts, e.g. $CaCO_3$, $CaSO_4$ "Ultrapure water" means water having a resistivity in the region of 18 MΩ cm. The stirring at room temperature is preferably maintained for a period of between 1 hour and 72 hours, for example for 48 hours. The nature of the stirring and the particle size of the calcium precursor may have an effect on the proportion of gem-bisphosphonic compound that may be grafted. It is thus preferable, when a given particle size has been selected for the calcium precursor, to adapt the stirring so as not to modify said particle size.

More preferably, the calcium precursor modified with a gem-bisphosphonic compound and used in the method according to the invention is calcium-deficient apatite (CDA), α-TCP, DCPD, or $CaCO_3$.

Cements

The present invention further relates to an injectable apatitic calcium-phosphate bone cement releasing a gem-bisphosphonic compound obtainable according to the method of the present invention as described above.

Calcium phosphate cements (CPC's) are materials consisting of a liquid phase being water or an aqueous solution and a pulverulent solid phase containing one or more solid compounds of calcium and/or phosphate salts so that if liquid and solid phases are mixed in an appropriate ratio they form a paste which at room or body temperature sets by precipitation of one or more other solid compounds, of which at least one is a calcium phosphate.

CPCs according to the invention are of the CDHA (calcium-deficient hydroxyapatite) type.

The CPC according to the invention is injectable. Indeed, in recent years, the occurrence of osteoporotic fractures has dramatically increased. Considering the lack of adequate treatment and the increasing number of elderly people, this trend is expected to continue. Osteoporotic fractures are often very difficult to repair, because the bone is very weak. It is therefore not possible to insert screws to hold osteosynthesis plates. A way to solve the problem is to inject a CPC into the osteoporotic bone to reinforce it.

Calcium and/or phosphate compounds useful in the invention as a component of the solid phase include hydroxyapatite (HA) $Ca_{10}(PO_4)_6(OH)_2$; amorphous calcium phosphate (ACP), $Ca_x(PO_4)y.H_2O$; monocalcium phosphate monohydrate (MCPM), $CaH_4(PO_4)_2.H_2O$; dicalcium phosphate dihydrate (DCPD), $CaHPO_4.2H_2O$, also called brushite; dicalcium phosphate anhydrous (DCPA), $CaHPO_4$; precipitated or calcium-deficient apatite (CDA), $(Ca,Na)_{10}(PO_4, HPO_4)_6(OH)_2$; alpha- or beta-tricalcium phosphate (α-TCP, β-TCP), $Ca_3(PO_4)_2$; tetracalcium phosphate (TTCP), $Ca_4P_2O_9$, and calcium carbonate, $CaCO_3$.

Easily resorbable calcium phosphate compounds are preferred.

A pulverulent solid phase comprising one or more calcium and/or phosphate compounds selected from the group consisting of HA, α-TCP, β-TCP, ACP, MCPM, DCPA, CDA, $CaCO_3$, and mixtures thereof, is preferred.

According to a particular embodiment, the solid phase can also comprise at least one synthetic polymer or biopolymer (e.g. HPMC).

A pulverulent solid phase comprising α-TCP is more preferred. α-TCP has the formula α-$Ca_3(PO_4)_2$. α-TCP is easily transformed into calcium-deficient hydroxyapatite (CDA) in aqueous solution. This property is used to form apatitic CPCs. An α-TCP preferred amount is comprised between 5% and 100%, more preferably 30% and 80%, and most preferably 30% and 70% of the solid phase.

A preferred pulverulent solid phase consists in a mixture of α-TCP, DCPA, CDA and $CaCO_3$.

Another preferred pulverulent solid phase consists in a mixture of α-TCP, DCPD, CDA, MCPM, and a biopolymer such as HPMC (hydroxypropylmethylcellulose).

The liquid phase may consist of one or more aqueous solutions containing one or several of the components of Table I, wherein said component may be chosen among the respective compounds are mixtures thereof shown in Table I.

TABLE I

| suitable liquid phases | |
|---|---|
| Component | Compounds |
| Sodium | NaF, NaCl, $Na_2CO_3$, $NaHCO_3$, $Na_2SO_4$, $Na_2SiO_3$, Na ortophosphates |
| Potassium | KF, $K_2CO_3$, $K_2SO_4$, KCl, $K_2SiO_3$, K ortophosphates |
| Magnesium | $MgHPO_4$, $Mg_3(PO_4)_2 \cdot xH_2O$, $MgF_2$, $MgCO_3$, MgO, $CaMg(CO_3)_2$, $Mg(OH)_2$ |
| Zinc | $Zn_3(PO_4)_2 \cdot xH_2O$, $ZnF_2$, $ZnCO_3$, $ZnSO_4$, ZnO, $Zn(OH)_2$, $ZnCl_2$ |
| Calcium | $Ca_5(PO_4)_3OH$, $CaSO_4$, $CaSO_4 \cdot \frac{1}{2}H_2O$, $CaSO_4 \cdot 2H_2O$, $CaF_2$, $CaCO_3$, $CaCl_2$ |
| Biopolymers | Proteins, peptides, proteoglycans, glycosaminoglycans, carbohydrates |
| Organic acids | Citric acid, malonic acid, pyruvic acid, tartaric acid |
| Inorganic acids | Phosphoric acid |
| Synthetic polymers | Polylactic acid, polyglycolic acid |
| Growth factors | TGF-β, osteocalcine, GLA proteins |

Preferably, the concentrations of aqueous solutions of the compounds described above as liquid phases are between about 0.1% and about 5% by weight.

A preferred liquid phase consists in a $Na_2HPO_4$ aqueous solution, a $NaH_2PO_4$ aqueous solution or a citric acid solution. More preferably, the liquid phase consists in a $Na_2HPO_4$ aqueous solution. For example, a solution of about 0.5% to about 5% by weight of $Na_2HPO_4$ in distilled water, a solution of about 0.5% to about 5% by weight of $NaH_2PO_4$ in distilled water or a solution of about 0.5% to about 5% by weight of citric acid in distilled water can be used.

The pH of the liquid phase should be between about 5 to about 10, preferably between about 5 and about 9, most preferably between about 5 and about 7.

Preferably, the liquid phase/solid phase (L/S) ratio is between about 0.20 to about 0.9 ml/g, more preferably between about 0.25 to about 0.8 ml/g, still preferably between about 0.25 to about 0.45 ml/g, the most preferably about 0.30 to about 0.45 ml/g.

Preferably, the liquid phase/solid phase (L/S) ratio is between about 0.25 ml/g and about 0.9 ml/g; more preferably between about 0.30 ml/g and about 0.45 ml/g, the liquid phase being an aqueous $Na_2HPO_4$ solution.

Preferably, the liquid phase/solid phase (L/S) ratio is between about 0.25 ml/g and about 0.9 ml/g; more preferably between about 0.30 ml/g and about 0.45 ml/g, the liquid phase being an aqueous $NaH_2PO_4$ solution.

Preferably, the liquid phase/solid phase (L/S) ratio is between about 0.20 ml/g and about 0.8 ml/g; more preferably between about 0.25 ml/g and about 0.30 ml/g, the liquid phase being an aqueous citric acid solution.

The setting time of a CPC depends on the composition of the powder and liquid components, the powder-to-liquid ratio, proportion of the calcium phosphate components and the particle sizes of the powder components. The setting time of the cement is an important property of the cement. If the setting time is too fast, the surgeon does not have time to use the cement before it is hard. If the setting time is too long, the surgeon must wait until he/she can close the wound.

The setting time is usually measured on a moulded sample with a Gillmore needle apparatus. This test basically measures when the hydrating cement paste develops some finite value of resistance to penetration. It defines an initial setting time and a final setting time based on the time at which a needle of particular size and weight either penetrates a cement paste sample to a given depth or fails to penetrate a cement paste sample. The Gillmore needle apparatus consists in two needles with a different diameter and a different weight. The first needle with the biggest diameter and the lowest weight measures the initial setting time and the second one with the lowest diameter and the highest weight measures the final setting time (C266 ASTM standard).

The initial setting time of the cement according to the invention is suitable for a chirurgical use, i.e. lower than 1 hour, preferably lower than about 45 min. Preferably, it is comprised between about 10 min and about 45 min, more preferably about 15 min and about 40 min, most preferably between about 20 min and about 35 min.

The final setting time of the cement according to the invention is comprised between about 40 min and about 3 h, preferably about 40 min and about 2 h, most preferably between about 40 min and about 1 h.

In a preferred embodiment, the compressive strength of the hardened cement according to the invention is above about 10 MPa, preferably above about 20 MPa.

In order to prevent any extravasation of the cement into the tissues surrounding bone, it is very important to visualise the cement. The easiest way is to increase the radio-opacity of the cement, for example by means of contrasting agents. For example, metallic powders of tantalum, titanium or tungsten can be used. It might be preferable to use liquid agents in partially bioresorbable cements, such as iodine compounds as iopamidol, iohexyl and iotrolan. Preferably, barium sulphate is used.

Uses

A further object of the invention is the use of an injectable CPC according to the invention to fill a bony defect or fracture caused by trauma, osteoporosis, osteolytic tumours, and articular or dental prostheses surgeries. This includes a surgery step but injectable CPCs according to the invention can get to inaccessible parts of the body and are suited for minimally invasive surgery procedures that are intended to reduce damage and pain while shortening the time before returning to function. This method of treatment comprises the introduction in the bony defect or fracture through a needle of an injectable CPC according to the invention.

For example, they can be employed in percutaneous vertebroplasty. This consists of a percutaneous puncture method to stabilize and straighten vertebral collapse of the thoracic and lumbar spinal column, most often as a result of osteoporosis.

In the course of osteoporosis, a very painful vertebral collapse can occur in the region of the thoracic (TSC) and lumbar (LSC) spinal column as a result of the reduced load-bearing capacity of the skeletal frame. This results in more or less distinct deformation of the vertebrae, and even in vertebral collapse. Both cases are easily recognizable by x-ray. Even a complete vertebral collapse and distinct deformation of the entire spinal column is possible.

Under local anesthetic, or, if desired, under full narcosis, a thin puncture needle is inserted to the vertebra, e.g. under x-ray guidance. At a certain point of the vertebra (the so-called pedicel), the bone can be punctured by the needle without risk. Afterwards, fluid bone cement is injected into the vertebra via the puncture needle; after the cement hardens, the vertebra is stabilized (vertebroplasty). If the vertebra is severely deformed (e.g. in the case of a wedge-like formation), the collapsed vertebra is straightened before the cement is injected. A balloon is hereby inserted into the vertebra via the puncture needle and inflated with fluid under high pressure. Following a successful straightening, the balloon is removed and the resulting cavity is filled with bone cement (balloon-kyphoplasty).

A further object of the invention is the use of an injectable CPC according to the invention to fill a tooth defect.

A supplementary object of the invention is a kit for preparing an injectable calcium-phosphate bone cement releasing a gem-bisphosphonic derivative according to any of claims 8 to 10 comprising a gem-bisphosphonic derivative or a calcium precursor modified with a gem-bisphosphonic compound, a solid phase and a liquid phase.

The invention will be further illustrated in view of the following figures and examples.

FIGURES

FIG. 1: $^{31}P$ VACP MAS NMR spectrum of modified CDA [10.4 wt % alendronate], showing the alendronate component associated to CDA (see example 1). The spectra were recorded at a spinning frequency of 12 kHz and a magnetic field of 7.0 T.

Figure 2:
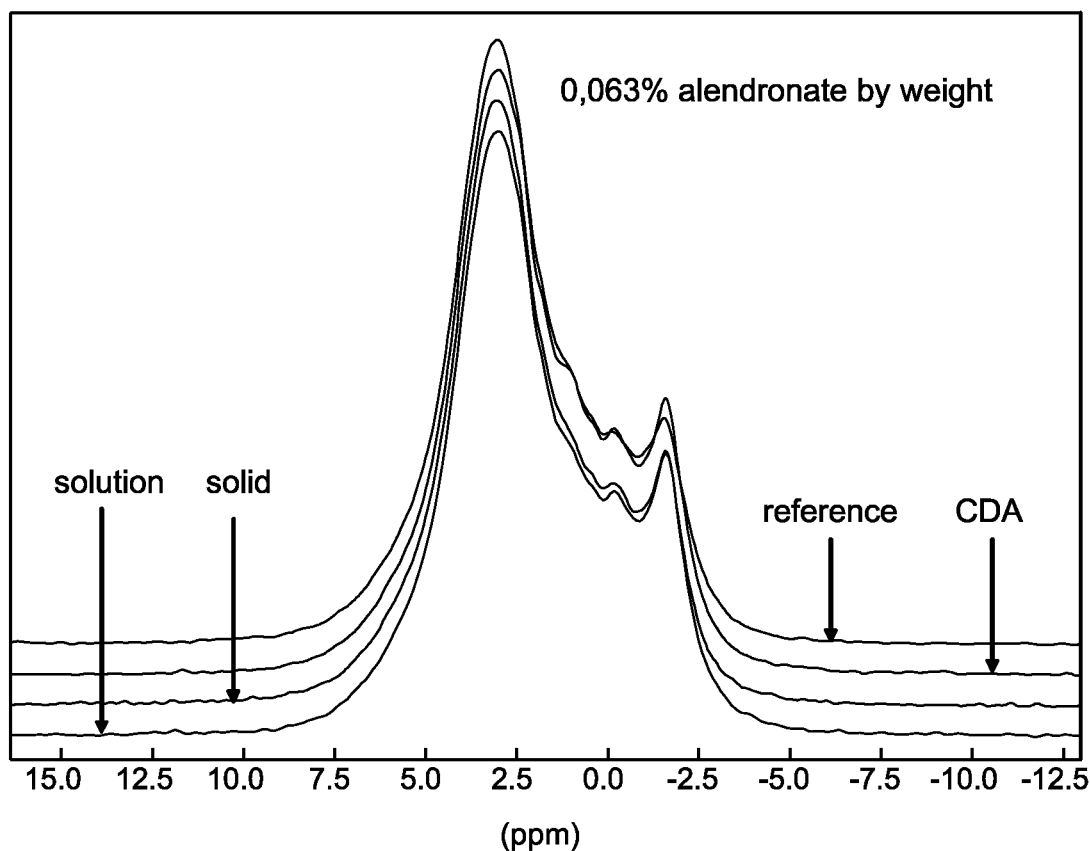
Figure 3:
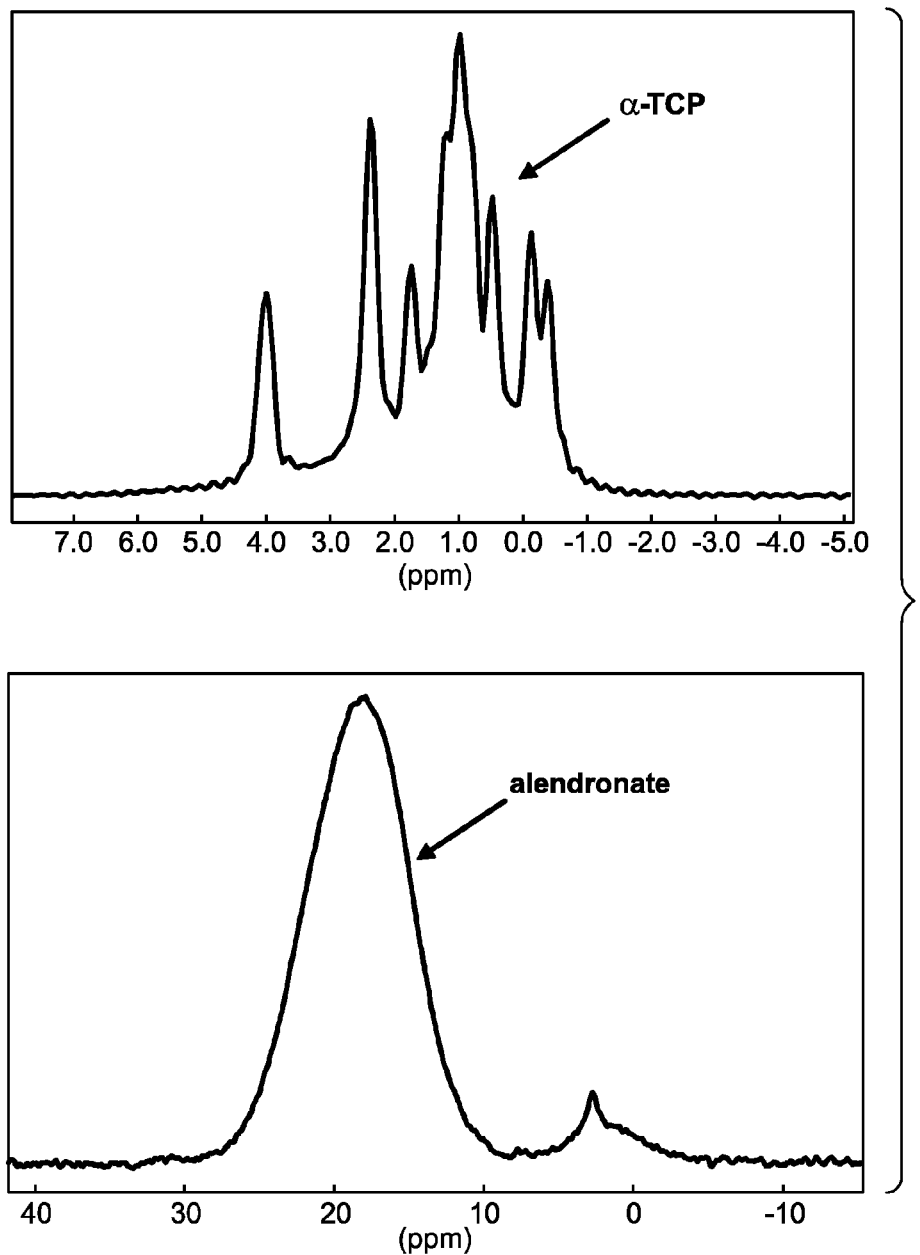

FIG. 2: $^{31}P$ MAS spectra of cements (see example 5) after a one week setting time. reference=no alendronate added, solid=alendronate powder mixed with the cement solid component, solution=alendronate dissolved in the cement liquid component, CDA=alendronate chemically associated to the CDA component FIG. 3: (upper view) $^{31}$P single pulse MAS-NMR spectrum of modified α-TCP [4.7 wt % alendronate], (bottom view) $^{31}$P VACP MAS NMR spectrum of modified α-TCP [4.7 wt % alendronate] (see example 2).

Figure 4:
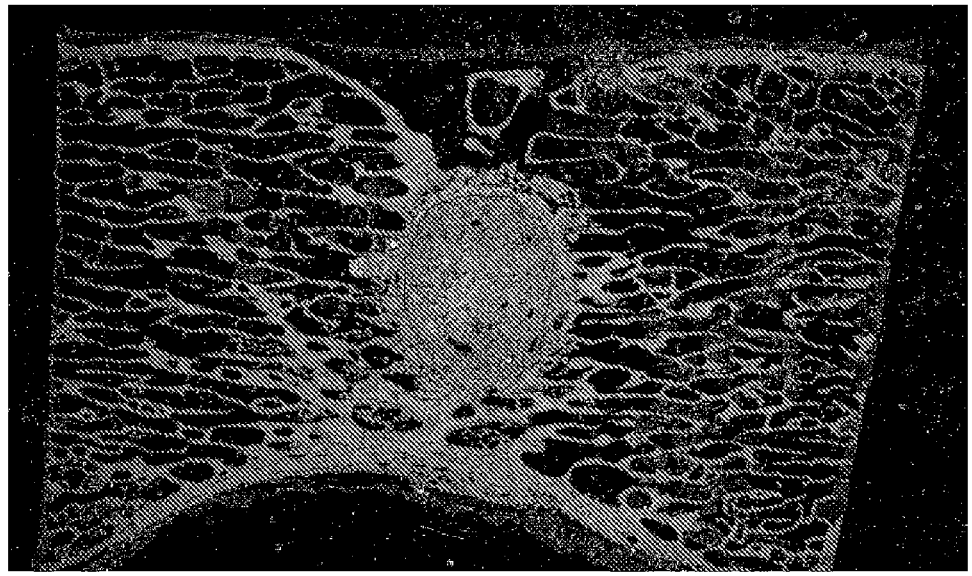

FIG. 4: Scanning Electron Microscopy (observation in the backscattered electron mode) view of a ewe vertebral body implanted with a 3 g-dose of unloaded CPC, 12 weeks after implantation.

Figure 5:
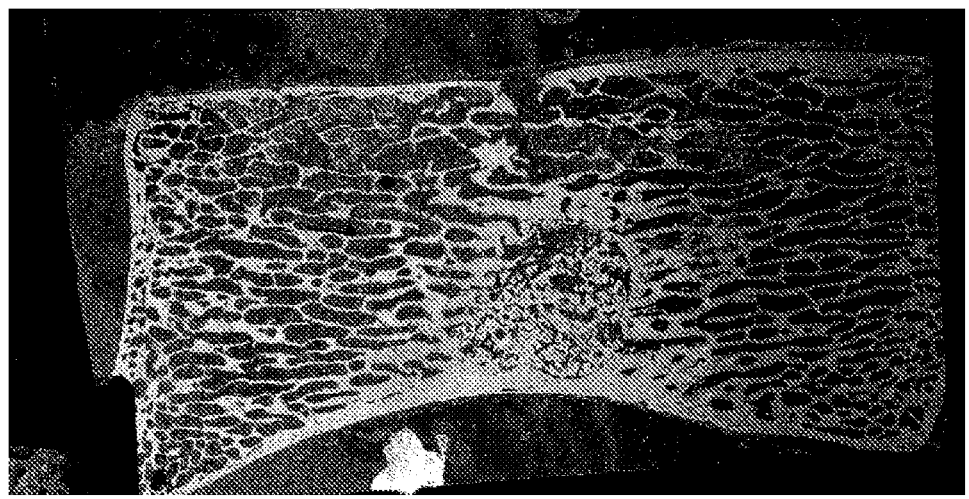

FIG. 5: Scanning Electron Microscopy (observation in the backscattered electron mode) view of a ewe vertebral body implanted with a 3 g-dose of alendronate-loaded CPC (0.13 wt %), 12 weeks after implantation (see example 8).

EXAMPLES

Example 1

Preparation of CDA Modified with Alendronate

A suspension of calcium phosphate was prepared by introducing 100 mg of CDA into 8.75 ml of ultrapure water mixed with 1.25 ml of a 0.02 mol.l$^{-1}$ sodium alendronate aqueous solution. The suspension was placed in a tube maintained at room temperature, and was stirred with a rotary stirrer at 16 rpm for 5 days. The suspension was then centrifuged and the most part of the supernatant was removed. The solid residue was filtered off, washed several times with small portions of ultrapure water, and then dried at room temperature. The resulting solid contained 7.4 wt % alendronate.

Example 2

Preparation of α-TCP Modified with Alendronate

In addition to example 1, the bisphosphonate can also be chemically associated to one of the other components of the solid phase (CaCO$_3$, DCPA, α-TCP . . . ). For example, in the case of α-TCP, a suspension of the calcium phosphate support was prepared by introducing 100 mg of α-TCP into 8.75 ml of ultrapure water mixed with 1.25 ml of a 0.02 mol.l$^{-1}$ sodium alendronate aqueous solution. The suspension was placed in a tube maintained at room temperature, and was stirred with a rotary stirrer at 16 rpm for 2 days. The suspension was then centrifuged and the most part of the supernatant was removed. The solid residue was filtered off, washed several times with small portions of ultrapure water, and then dried at room temperature. The resulting solid contained 4.7 wt % alendronate.

Example 3

Preparation of DCPD Modified with Alendronate

In addition to example 1, the bisphosphonate can also be chemically associated to one of the other components of the solid phase. For example, in the case of DCPD, a suspension of the calcium phosphate support was prepared by introducing 100 mg of DCPD into 9 ml of ultrapure water mixed with 1 ml of a 0.02 mol.l$^{-1}$ sodium alendronate aqueous solution. The suspension was placed in a tube maintained at room temperature, and was stirred with a rotary stirrer at 16 rpm for 2 days. The suspension was then centrifuged and the most part of the supernatant was removed. The solid residue was filtered off, washed several times with small portions of ultrapure water, and then dried at room temperature. The resulting solid contained 5.3 wt % alendronate.

Example 4

Preparation of CaCO$_3$ Modified with Alendronate

In addition to example 1, the bisphosphonate can also be chemically associated to one of the other components of the solid phase. For example, in the case of CaCO$_3$, a suspension of the calcium phosphate support was prepared by introducing 100 mg of CaCO$_3$ into 8.5 ml of ultrapure water mixed with 1.5 ml of a 0.02 mol.l$^{-1}$ sodium alendronate aqueous solution. The suspension was placed in a tube maintained at room temperature, and was stirred with a rotary stirrer at 16 rpm for 2 days. The suspension was then centrifuged and the most part of the supernatant was removed. The solid residue was filtered off, washed several times with small portions of ultrapure water, and then dried at room temperature. The resulting solid contained 5.0 wt % alendronate.

Example 5

Preparation of an Injectable CPC Releasing Alendronate

The solid phase of the cement consists of alpha-tertiary calcium phosphate α-TCP, CaHPO$_4$, CaCO$_3$ and some precipitated hydroxyapatite CDA.

The solid phase composition is the same for all samples
62.4 wt % (249.6 mg) α-TCP
26.8 wt % (107.2 mg) DCPA (CaHPO$_4$)
8.8 wt % (35.2 mg) CaCO$_3$
2 wt % (8 mg) CDA.

α-TCP was prepared by using an appropriate mixture of CaHPO$_4$ and CaCO$_3$, heating it at 1300° C. for at least 6 h and quenching it in air down to room temperature.

Three ways are used to combine alendronate with the cement samples.
- alendronate is dissolved in the cement liquid phase (up to 1.2 mg in 120 µL see Table IV); or
- alendronate is added to the solid phase (0.1-10 mg for 400 mg see Table IV); or
- alendronate is chemically associated to (i) CDA as prepared in Example 1 replacing partially the CDA of the solid phase (see Table II) (ii) α-TCP as prepared in Example 2 replacing partially the α-TCP of the solid phase (see Table III).

Seven concentrations of alendronate have been used:
0.100 wt % (0.40 mg)
0.060 wt % (0.25 mg)
0.025 wt % (0.10 mg)
0.25 wt % (1 mg)
0.3 wt % (1.2 mg)
2.5 wt % (10 mg)
3.9 wt % (15.7 mg)

Three liquid phases were chosen to prepare different cement formulations: 2.5% Na$_2$HPO$_4$ by weight in water, 2.5% NaH$_2$PO$_4$ by weight in water or 85 mM citric acid in water.

The liquid/powder ratio L/P of cements was taken to be either 0.30 ml/g for samples prepared with Na$_2$HPO$_4$ and NaH$_2$PO$_4$ and 0.25 ml/g for samples prepared with citric acid.

The powders were finely ground during 10 minutes.

Then, the liquid phase is added dropwise and the two phases are mixed with a spatula or a pestle.

The mixing sets in moulds.

Example 6

Setting Time Assays of the Samples of Example 5

Setting times were determined with Gillmore needles following the standard ASTM C266-89.

Tables II and III and IV summarize the results.

TABLE II

Initial and final setting times with alendronate chemically associated to CDA

| Liquid phase | m (Alend) [mg] | pH | ti [min] | tf [min] | ti [min] | tf [min] | T [°C.] |
|---|---|---|---|---|---|---|---|
| Na$_2$HPO$_4$ | control | 8.5 | 30 | 75 | | | 20 |
| (2.5% by | 0.1 | 8.5 | 30 | 80 | 30 | 70 | 20 |
| weight) | 0.25 | 8.5 | 40 | 90 | 30-35 | 80 | 20 |
| L/S = 0.3 | 0.5 | 8.5 | 40 | 85 | 35 | 75 | 20 |
| NaH$_2$PO$_4$ | control | 5 | 20 | 60 | | | 21 |
| (2.5% by | 0.1 | 4.5 | 20 | 60 | 20 | 60 | 21 |
| weight) | 0.25 | 4.5 | 20 | 60 | 20 | 60 | 21 |
| L/S = 0.3 | 0.5 | 4.5 | 25 | 80 | 20 | 60 | 21 |

Table III: Initial and final setting times with alendronate chemically associated to α-TCP

TABLE III

Initial and final setting times with alendronate chemically associated to α-TCP

| Liquid phase | m (Alend) [mg] | pH | ti [min] | tf [min] | T [°C.] |
|---|---|---|---|---|---|
| NaH$_2$PO$_4$ | control | 5 | 20 | 60 | 21 |
| (2.5% by weight) | 0.5 obtained by mixing 4.24 wt % of modified α-TCP [4.7 wt % alendronate] in pure α-TCP$^a$ | 5 | 30 | 70 | 21 |
| L/S = 0.3 | 0.5 obtained by using only modified α-TCP [0.2 wt % alendronate]$^b$ | 5 | 35 | 70 | 21 |
| | 1 obtained by mixing 8.48 wt % of modified α-TCP [4.7 wt % alendronate] in pure α-TCP$^c$ | 5 | 35 | 70 | 21 |
| | 10 obtained by using only modified α-TCP [4 wt % alendronate]$^d$ | 5 | 35 | 85 | 21 |

Note
$^a$After one week incubation, a full transformation of α-TCP was observed, and the resulting cement showed good mechanical properties.
Note
$^b$After one week incubation, the self-setting of the cement was very poor, while X-Ray diffraction gave evidence that the transformation of α-TCP was very low.
Note
$^c$After one week incubation, a full transformation of α-TCP was observed, and the resulting cement showed quite good mechanical properties, although the cement was a little more crumby than in the case of note a.
Note
$^d$After one week incubation, the self-setting of the cement was very poor, while X-Ray diffraction gave evidence that the transformation of α-TCP was very low. From notes b and d, it can be deduced that if the entire α-TCP component is modified with a bisphosphonate, the self-setting properties of the cement are strongly inhibited.

TABLE IV

Initial and final setting times with alendronate dissolved in the liquid phase or added to the solid phase
T = 22° C.

| | | Alendronate dissolved in the liquid phase | | | Alendronate added to the solid phase | | |
|---|---|---|---|---|---|---|---|
| Liquid phase | m (Alend) [mg] | pH | ti [min] | tf [min] | pH | ti [min] | tf [min] |
| Na$_2$HPO$_4$ | control | 8.5 | 25-30 | 75 | 8.5 | 25-30 | 75 |
| (2.5% by | 0.4 | 6.5-7.0 | 45 | 80 | 8.5 | 35 | 95 |
| weight) | 0.25 | 6.5-7.0 | 45 | 80 | 8.5 | 40 | 90 |
| L/S = 0.3 | 0.1 | 6.5-7.0 | 40 | 90 | 8.5 | 30 | 95 |
| **NaH$_2$PO$_4$ | control | 5 | 25 | 65-70 | 5 | 25 | 65-70 |
| (2.5% by | 10$^a$ | | | | 5 | 45 | 95 |
| weight) | 1.2$^b$ | 4.5 | 65 | >100 | | | |
| L/S = 0.3 | 0.4 | 4.5 | 35 | 75 | 5 | 30 | 80 |
| | 0.25 | 4.5 | 45 | 90 | 5 | 30 | 80-85 |
| | 0.1 | 4.5 | 35 | 60 | 5 | 35 | 80 |
| citric acid$^c$ | control | 2 | 12 | 53 | 2 | 12 | 53 |
| (85 mM) | 0.4 | 2 | 35 | 65 | 2 | 13 | 60 |
| L/S = 0.25 | 0.25 | 2 | 20 | 55 | 2 | 15 | 60 |
| | 0.1 | 2 | 25 | 55 | 2 | 15 | 60 |

Note
$^a$In that case, the amount of α-TCP transformed is low, and after one week incubation, the material is obtained as a chewy paste with poor mechanical properties.
Note
$^b$In that case, the amount of α-TCP transformed is low, and after one week incubation, the material is obtained as a soft paste with very poor mechanical properties.
Note
$^c$Under incubation conditions, a swelling of the preparation is observed, and after one week poor mechanical properties were observed for the material that is brittle and crumby, although a full transformation of α-TCP was evidenced by X-ray diffraction.

Example 7

RMN Assays (Concerning the Samples of Example 5)

The cement samples obtained after 7 days incubation were studied using solid-state magic angle spinning (MAS) NMR spectrometry. The experiments were carried out on a Bruker Advance 300 spectrometer, operating at 7.0 T ($^1$H and $^{31}$P Larmor frequencies of 300 and 121.5 MHz), using 4 mm double-resonance and triple-resonance MAS probes.

The $^{31}$P-{$^1$H} cross-polarisation (CP) MAS experiments were performed using a ramped cross polarization with a contact time of 1 ms. $^1$H decoupling was achieved using the SPINAL64 sequence with a $^1$H nutation frequency of 70 kHz. The recycle delay was set to 2 s. Longitudinal relaxation times $T_1$ for $^{31}$P sites in the modified α-TCP samples were measured and found to vary between 10 and 300 s ($v_0$($^{31}$P)=121.5 MHz). The $^{31}$P single pulse spectra were thus obtained by recording a single scan after a delay of 600 s.

Example 8

Preparation of a Second Type of Injectable CPC Releasing Alendronate

The solid phase of the cement consists of alpha-tertiary calcium phosphate α-TCP, DCPD, MCPM, HPMC and some precipitated hydroxyapatite CDA.
The solid phase composition is the same for all samples:
78 wt % (7.8 g) α-TCP
5 wt % (0.5 g) DCPD (CaHPO$_4$.2H$_2$O)
5 wt % (0.5 g) MCPM (Ca(H$_2$PO$_4$)$_2$.H$_2$O)
10 wt % (1 g) CDA.
2 wt % (0.2 g) HPMC (hydroxypropylmethylcellulose).

α-TCP was prepared by using an appropriate mixture of CaHPO$_4$ and CaCO$_3$, heating it at 1300° C. for at least 6 h and quenching it in air down to room temperature.

Three ways are used to combine alendronate with the cement samples.

alendronate is dissolved in the cement liquid phase (up to 40 mg in 5 mL see Table V)

alendronate is added to the solid phase (13.3-40 mg for 10 g see Table V)

alendronate is chemically associated to (i) CDA as prepared in Example 1 replacing partially the CDA of the solid phase (see Table VI) (ii) α-TCP as prepared in Example 2 replacing partially the α-TCP of the solid phase (see Table VII) (iii) DCPD as prepared in Example 3 replacing partially the DCPD of the solid phase (see Table VIII)

Three concentrations of alendronate have been used:

0.133 wt % (13.3 mg)
0.266 wt % (26.6 mg)
0.4 wt % (40.0 mg)

The liquid phase chosen to prepare different cement formulations was 5% Na$_2$HPO$_4$ by weight in water. The liquid/powder ratio L/P of cements was taken to be 0.50 ml/g.

The powders are finely ground during 30 minutes.

Then, the liquid phase is added dropwise and the two phases are mixed with a spatula or a pestle.

The mixing sets in moulds.

Example 9

Setting Time Assays Related to Example 8

The properties of the cements were studied using Vickers microindentation (maximal compressive strength), powder X-ray diffraction and $^{31}$P solid state NMR (transformation ratio of α-TCP to CDA), and texture analyses (evaluation of the initial setting time). The latter method consists in measuring the compression force necessary to extrude the cement dough (initial setting time=the time to reach a force value>25 Newton) versus time.

Tables V, VI, VII and VIII summarize the results.

TABLE V

Setting and mechanical properties of cements with alendronate dissolved in the liquid phase or added to the solid phase

| m(Alend) [mg] | Maximal compressive strength [MPa] | Initial setting time [min] | Transformation of α-TCP to CDA |
|---|---|---|---|
| Alendronate dissolved in the liquid phase ||||
| 0 (control) | 11 ± 1 | 15 | high |
| 13.3 | 18 ± 3 | 65 | high |
| 26.6 | 19 ± 1 | >100 | high |
| 40[b] | 20 ± 3 | >>250 | high |
| Alendronate added to the solid phase ||||
| 0 (control) | 11 ± 1 | 15 | high |
| 13.3 | 11 ± 1 | 45 | high |
| 26.6 | Not measurable[a] | >100 | high |
| 40[b] | Not measurable[a] | >>100 | Very high |

Note
[a]in that case, after two days incubation, the material is obtained as a brittle and crumby material, leading to non-reproducible data.

Note
[b]the presence of alendronate is detected on $^{31}$P-$^1$H VACP NMR spectra, as a broad signal at ca. 18 ppm, very similar to that present in FIG. 1, thus suggesting that the bisphosphonate is chemisorbed on the surface of the CDA resulting from the transformation of the α-TCP component.

TABLE VI

Setting and mechanical properties of cements with alendronate chemically associated to CDA

| | Alendronate associated to CDA |||
|---|---|---|---|
| m(Alend) [mg] | Maximal compressive strength [MPa] | Initial setting time [min] | Transformation of α-TCP to CDA |
| 0 (control) | 11 ± 1 | 15 | high |
| 13.3 | 16 ± 2 | 40 | high |
| 26.6 | 19 ± 2 | 90-100 | high |
| 40[a] | 18 ± 2 | >>90 | high |

Note
[a]The presence of alendronate is detected on $^{31}$P-$^1$H VACP NMR spectra, as a broad signal at ca. 18 ppm, very similar to that present in FIG. 1, thus suggesting that the bisphosphonate is chemisorbed on the surface of the CDA resulting from the transformation of the α-TCP component.

TABLE VII

Setting and mechanical properties of cements with alendronate chemically associated to α-TCP.

| | Alendronate associated to α-TCP |||
|---|---|---|---|
| m(Alend) [mg] | Maximal compressive strength [MPa] | Initial setting time [min] | Transformation of α-TCP to CDA |
| 0 (control) | 11 ± 1 | 15 | high |
| 13.3 | 13 ± 1 | 40 | high |
| 26.6 | 12 ± 1 | >120 | high |
| 40 | 12 ± 1 | >>120 | high |
| 13.3, obtained by mixing 6 wt % of modified α-TCP [2.85 wt % alendronate] in pure α-TCP | 14 ± 1 | 17 | high |
| 26.6, obtained by mixing 12 wt % of modified α-TCP [2.85 wt % alendronate] in pure α-TCP | 14 ± 1 | 30 | high |
| 40, obtained by mixing 18 wt % of modified α-TCP [2.85 wt % alendronate] in pure α-TCP | 15 ± 1 | 75 | high |

TABLE VIII

Setting and mechanical properties of cements with alendronate chemically associated to DCPD.

| | Alendronate associated to DCPD |||
|---|---|---|---|
| m(Alend) [mg] | Maximal compressive strength [MPa] | Initial setting time [min] | Transformation of α-TCP to CDA |
| 0 (control) | 11 ± 1 | 15 | high |
| 13.3 | 22 ± 3 | 60 | high |
| 26.6 | 20 ± 1 | >>90 | high |
| 40 | 20 ± 2 | >>90 | high |

For the different cases corresponding to Tables V-VIII (0.133 wt % alendronate relative to the solid phase), cement blocks obtained after 2 hours incubation were immerged in a 0.9 wt % NaCl aqueous solution at 37° C. for 5 days. The blocks were then dried and cut, before SEM (Scanning Electron microscopy) observations. In all cases, homogeneously dispersed macropores (20 to 100 μm) were observed, resulting from the degradation of the HPMC component.

Example 10

In Vivo Assays in Ewes Related to Example 8

Six 10-years-old ewes are used for this experiment. The animals had free access to normal diet. The animals were randomly implanted with alendronate-loaded or unloaded CPC. 3 g-doses of alendronate-loaded CPC were prepared according to example 8 with 4 mg of alendronate chemically associated to CDA (see example 1). Each ewe received 3×3 g-doses (shared inside 3 vertebral bodies) of either alendronate-loaded or unloaded CPC. Animals were sacrificed 3 months after implantation. Each implanted vertebral body was analysed using:
1. Scanning Electron Microscopy (observation in the backscattered electron mode)
2. Micro-CT scan (histomorphometric measurements).

Auto-induced macroporosity, direct interface with bone and significant surface osteoconduction were observed on SEM images in both CPC and alendronate-loaded CPC (FIGS. 4 and 5). Significant implant resorption and volumic osteoconduction were observed for alendronate-loaded CPC implants (FIG. 5). Comparative histomorphometric analysis of the trabecular bone structures surrounding CPC and alendronate-loaded CPC implants demonstrated (N=18, p<0.05) clearly that the bone architecture is reinforced by alendronate-loaded CPC implants (see table below).

|   | Bone Volume (%) | Trabecular space (μm) | Trabecular number (μm$^{-1}$) |
|---|---|---|---|
| CPC | 17.7 ± 1.5 | 494.9 ± 5.8 | 0.95 ± 0.07 |
| CPC + alendronate | 28.4 ± 2.7 | 420.7 ± 8.0 | 1.53 ± 0.22 |

The invention claimed is:

1. A method for preparing an injectable calcium-phosphate bone cement, wherein said bone cement releases a gem-bisphosphonic compound, said method comprising:
adding a calcium-deficient apatite (CDA) modified with a bisphosphonic acid or salt thereof to a cement solid phase, wherein said calcium-phosphate bone cement has an initial setting time lower than 1 hour, and wherein the amount of the bisphosphonic acid or a salt thereof is up to 0.15% by weight with respect to the weight of solid phase.

2. The method according to claim 1, wherein the bisphosphonic acid or salt thereof is selected in the group consisting of etidronate, clodronate, pamidronate, alendronate, risedronate, tiludronate, ibandronate, zoledronate, incadronate, olpadronate, and neridronate.

3. The method according to claim 1, wherein the bisphosphonic acid or salt thereof is alendronate.

4. The method according to claim 1, wherein the calcium solid precursor further comprises one or more selected from the group consisting of: α-tricalcium phosphate, (α-TCP), dicalcium phosphate dehydrate (DCPD), and $CaCO_3$.

5. The method according to claim 1, wherein the solid phase comprises one or more calcium and/or phosphate compounds selected from the group consisting of hydroxyapatite (HA), α-TCP, β-tricalcium phosphate (β-TCP), amorphous calcium phosphate (ACP), monocalcium phosphate monohydrate (MCPM), dicalcium phosphate anhydrous (DCPA), CDA, CaCO3 and mixtures thereof.

6. The method according to claim 1, wherein the solid phase also comprises at least one synthetic polymer or biopolymer.

7. The method according to claim 1, wherein the injectable cement comprises a liquid phase selected from the group consisting of a $Na_2HPO_4$ aqueous solution, a $NaH_2PO_4$ aqueous solution or a citric acid aqueous solution.

8. The method according to claim 7, wherein the liquid phase consists in a $NaH_2PO_4$ aqueous solution.

9. The method according to claim 7, wherein the pH of the liquid phase is from 5 to 10.

10. The method according to claim 7, wherein the injectable cement comprises a liquid phase/solid phase (L/S) ratio from 0.20 to 0.9 ml/g.

* * * * *